United States Patent
Brown et al.

(10) Patent No.: US 9,089,377 B2
(45) Date of Patent: Jul. 28, 2015

(54) BONE SCREW

(75) Inventors: Scott C. Brown, Warsaw, IN (US); Nick Deeter, Warsaw, IN (US); Gary Barnett, Warsaw, IN (US); Anthony McPherron, Plymouth, IN (US); David W. Daniels, Winona Lake, IN (US)

(73) Assignee: Orthopediatrics Corp., Warsaw, IN (US)

( * ) Notice: Subject to any disclaimer, the term of this patent is extended or adjusted under 35 U.S.C. 154(b) by 386 days.

(21) Appl. No.: 12/390,815

(22) Filed: Feb. 23, 2009

(65) Prior Publication Data

US 2010/0217329 A1 Aug. 26, 2010

(51) Int. Cl.
*A61B 17/86* (2006.01)
*A61B 17/74* (2006.01)

(52) U.S. Cl.
CPC ........... *A61B 17/8605* (2013.01); *A61B 17/742* (2013.01); *A61B 17/8685* (2013.01); *A61B 17/864* (2013.01)

(58) Field of Classification Search
CPC ............. A61B 17/8685; A61B 17/742; A61B 17/8605
USPC ............. 606/315, 72, 73, 217, 219, 323, 328, 606/71, 300–312, 317, 319–320
See application file for complete search history.

(56) References Cited

U.S. PATENT DOCUMENTS

| | | | | |
|---|---|---|---|---|
| 3,343,443 A * | 9/1967 | Moore | ............... | 411/5 |
| 4,059,102 A * | 11/1977 | Devas | ........................... | 606/309 |
| 4,432,358 A * | 2/1984 | Fixel | ............................... | 606/66 |
| 5,409,489 A | 4/1995 | Sioufi | | |
| 5,569,251 A * | 10/1996 | Baker et al. | ................... | 606/281 |
| 5,693,055 A | 12/1997 | Zahiri et al. | | |
| 5,738,685 A * | 4/1998 | Halm et al. | ................... | 606/270 |
| 5,743,912 A | 4/1998 | Lahille et al. | | |
| 5,951,560 A * | 9/1999 | Simon et al. | .................. | 606/304 |
| 5,997,541 A * | 12/1999 | Schenk | ........................ | 606/303 |
| 6,319,254 B1 * | 11/2001 | Giet et al. | ..................... | 606/916 |
| 6,436,100 B1 * | 8/2002 | Berger | .......................... | 606/916 |
| 6,517,543 B1 * | 2/2003 | Berrevoets et al. | ........... | 606/304 |
| 7,094,236 B2 | 8/2006 | Waisman | | |
| 7,503,919 B2 | 3/2009 | Shaw | | |
| 7,666,212 B2 | 2/2010 | Pathak | | |
| 8,403,972 B2 * | 3/2013 | Hasenbohler et al. | ........ | 606/309 |
| 2002/0016594 A1 * | 2/2002 | Schlapfer et al. | ............... | 606/73 |
| 2003/0171754 A1 * | 9/2003 | Del Medico | ..................... | 606/69 |
| 2004/0210227 A1 * | 10/2004 | Trail et al. | ....................... | 606/73 |
| 2005/0010226 A1 * | 1/2005 | Grady et al. | ..................... | 606/69 |
| 2005/0240188 A1 * | 10/2005 | Chow et al. | ..................... | 606/72 |
| 2005/0240198 A1 * | 10/2005 | Albertson et al. | ............ | 606/103 |
| 2006/0106390 A1 * | 5/2006 | Jensen et al. | ..................... | 606/73 |
| 2008/0086129 A1 * | 4/2008 | Lindemann et al. | ............ | 606/61 |
| 2008/0255621 A1 * | 10/2008 | Fricker et al. | ................. | 606/302 |
| 2008/0299516 A1 * | 12/2008 | Aldecoa | ........................ | 433/174 |
| 2010/0016903 A1 * | 1/2010 | Matityahu et al. | ............. | 606/301 |

* cited by examiner

*Primary Examiner* — David Bates
*Assistant Examiner* — Samuel Hanna
(74) *Attorney, Agent, or Firm* — Woodard, Emhardt, Moriarty, McNett & Henry LLP

(57) ABSTRACT

There are disclosed embodiments of screws for use in orthopedic surgery, particularly in pediatric patients. In some embodiments, inner and outer implantable members are provided, with the outer implantable member threadable on the inner implantable member to provide compression on two or more bone parts. In some embodiments, screw members are provided with a threaded shaft, and the thread continues into the head of the screw member to enable the thread to remain in pediatric bone.

28 Claims, 9 Drawing Sheets

BONE SCREW

The present disclosure relates to orthopedic surgical implants, particularly those suited for use in specialized pediatric cases. In particular, the present disclosure concerns bone screws useful for insertion into and/or compression of bones or bone parts to treat fractures, trauma or other maladies.

BACKGROUND

In the field of orthopedic surgery, numerous implant devices are known for a variety of therapeutic or corrective purposes. Among these types of implants are screws, plates, cables, and other devices for joining two pieces of bone or adding support to assist in healing a fracture in a bone. These and other devices hold the bone or bone pieces in a stable position so that healing in the form of bone growth to rejoin bone across a fracture or to rejoin pieces that have become separated can occur.

In implanting such corrective or therapeutic devices, the most common techniques include open surgical approaches with retraction of soft tissues adjacent the bone or bone pieces and percutaneous, small-incision approaches. The bone tissue is then manipulated with instruments or by hand so that they are positioned as the surgeon desires, most often in a naturally-occurring position for the tissue. For example, where a fracture exists in a bone, the bone on each side of the fracture is moved so as to partially or completely close the fracture. If there are separated fragments or comminuted bone between larger fragments, then the fragments may be repositioned to approximate their natural place before supporting and/or connecting implants are placed. Once implant(s) are placed so as to promote healing, the surgery can be concluded with repair of soft tissues and closing of the surgical access.

In such procedures, a number of steps and devices are required. Reduction of the number of steps and the instruments needed to accomplish rejoinder or healing would result in a shorter, easier operation. Savings of time and effort generate a potential for cost reduction, a generally less traumatic surgery for the patient and thus a relatively easier recovery, and less opportunity for error by the surgeon. Further, existing devices are generally intended for use in adult anatomy. For pediatric cases, commonly only the size of implant devices are changed, while their substantial operating characteristics remain the same. Devices and methods that accomplish such goals and/or are suited to the special needs of pediatric patients remain needed.

SUMMARY

Among other things, there is disclosed an orthopedic implant device for compressing bone parts toward each other, including a first implantable member having a shaft and a head, with the shaft having an external thread adapted for anchoring in a first bone part. The first implantable member may have a central longitudinal cannula extending through the shaft and the head, with the cannula having an internal thread. A second implantable member having an elongated distal portion and a proximal end is also included. The distal portion has an external thread engaged with the internal thread of the first implantable member's cannula, and a distal end extending from the first implantable member and adapted to anchor in a second bone part. Turning the first implantable member threads it into the first bone part as well as threading it along the second implantable member, moving the distal end of the second implantable member toward the first implantable member.

In various embodiments, the external thread of the first implantable member has a first pitch, and the internal thread of the first implantable member's cannula and the external thread of the second implantable member each have a second pitch that is unequal to the first pitch. The first pitch may be greater than the second pitch, and the second pitch may be a predetermined fraction of the first pitch (or the first pitch may be an integer multiple of the second pitch). The external thread of the first implantable member may extend from the shaft into the head. In one particular such example, the head has an outer surface that tapers outwardly from the shaft so that the head's diameter gets larger from the shaft's diameter. The first implantable member's external thread has a crest diameter and a root diameter, and the crest diameter remains substantially constant from the shaft into the head, while the root diameter enlarges substantially uniformly from the shaft as it winds around the head, so that the root diameter and crest diameter coincide at a portion of the head's outer surface. The second implantable member may be a variety of elongated items, such as a rod or a flexible wire. In some embodiments, the external thread of the first implantable member is a cancellous thread, and the internal thread of the first implantable member and the external thread of the second implantable member are machine threads. One or both of the implantable members may be resorbable.

Also disclosed herein are methods, including methods of moving two bone parts toward each other. For example, one can provide a device as described herein. A hole can be prepared through a first bone part that is of a size to accommodate the first implantable member. The second implantable member is inserted through the hole and into a second bone part so that a distal end of the second implantable member is securely anchored in the second bone part, and the first implantable member is threaded onto the second implantable member and into the hole in the first bone part. The first implantable member enters the first bone part and the second implantable member moves with respect to the first implantable member to draw the distal part of the second implantable member toward the first implantable member, thereby drawing the bone parts together.

The disclosure also includes an orthopedic implant system that includes a one-piece implantable screw having a shaft, a head with an external surface, and a transition between head and shaft. The screw includes an external thread adapted to be threaded into bone and extending along the entire length of the shaft, through the transition and at least partially along the head portion. The external thread has a crest with a constant crest diameter and a root with a root diameter that is constant along the shaft and uniformly increasing in the transition, so that the root diameter and the crest diameter coincide at a location on the screw, and the outer surface of the head has a diameter larger than the crest diameter. It will be seen that particular embodiments may be cannulated or solid (e.g. non-cannulated), may include cortical and/or cancellous threads, and may be self-tapping or otherwise.

In some embodiments, the screw includes a distal end of the shaft and a proximal end of the head, with that distal end having a first central opening and that proximal end having a second central opening larger in diameter than the first central opening, and a cannula which may be internally-threaded connecting the first and second openings. An implant can be included that has an external thread that is threadable within the cannula's internal thread. The implant may have a distal end including an anchor portion to hold the distal end within bone, with the distal end of the implant extending beyond the distal end of the screw's shaft. The anchor portion can include an external thread adapted for threading into bone, and the implant can include a driving head for imparting rotation to the implant and threading the anchor portion into bone. Such anchor portion may include a barb.

In the screw, the second central opening may include an internal print for accommodating a driving tool and a non-threaded tapering passage between that internal print and the internal thread in the cannula. The head may have a maximum diameter that is about twice the root diameter in the shaft.

Embodiments of outer screws or implantable members may be used for holding implants to bone as well. Such implants may include stabilization plates.

The inventors have discovered that implants created for and used in orthopedic procedures for adults can be unsuitable or create difficulties for use in pediatric patients. The physical structure of pediatric bones and the process of growth in them create special conditions that are not adequately addressed by devices for adult use, even if those devices are cut down in size. As will be explained further below, pediatric orthopedic surgery frequently faces questions of securing bone fragments (as opposed to potentially removing such fragments in adult patients) and removing implants easily (as opposed to allowing the implants to remain in adult patients).

DESCRIPTION OF THE ILLUSTRATED EMBODIMENTS

Figure 1B:
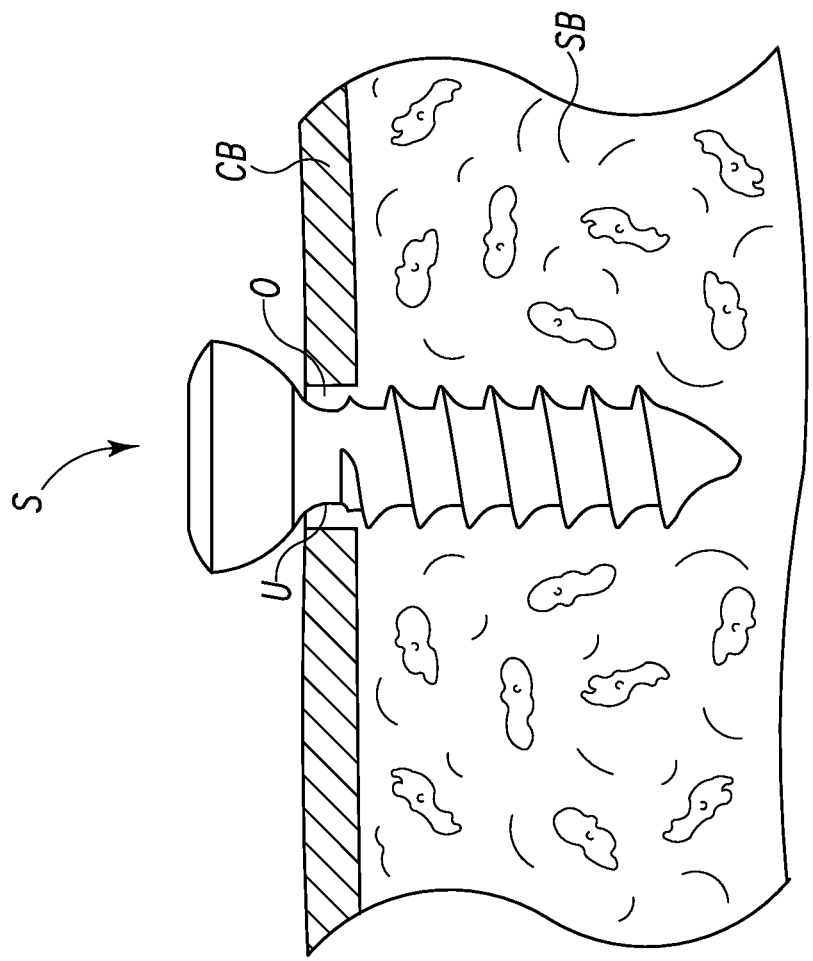
FIG. 1B is a part cross-sectional representation of the screw of FIG. 1 inserted in pediatric bone.

For the purposes of promoting an understanding of the principles of the disclosure, reference will now be made to the embodiment illustrated in the drawings and specific language will be used to describe the same. It will nevertheless be understood that no limitation of the scope of the claims is thereby intended, such alterations and further modifications in the illustrated device, and such further applications of the principles of the disclosure as illustrated therein, being contemplated as would normally occur to one skilled in the art to which the disclosure relates.

Figure 1A:
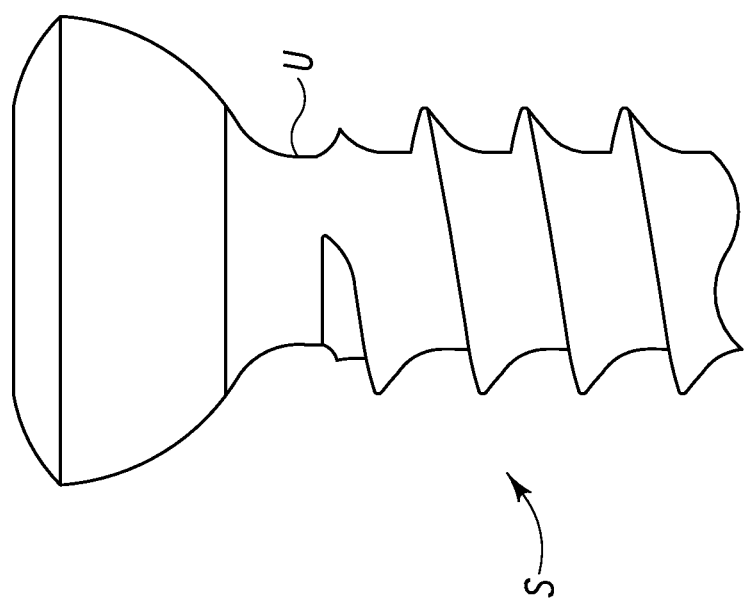
FIG. 1A is a side representation of an existing bone screw for orthopedic use.

FIG. 1A shows generally a known type of bone screw S, having a threaded shaft and a head with a lower uniform spherical surface, and FIG. 1B represents its implantation in pediatric bone. The bone includes a layer of cortical bone CB and the inner cancellous or spongy bone SB. Referring now generally to the remainder of the drawings, there is shown a bone screw 20 according to the present disclosure. Particular embodiments of bone screw 20 may be used as a compression screw or as an anchoring screw, as will be described further below.

Figure 5:
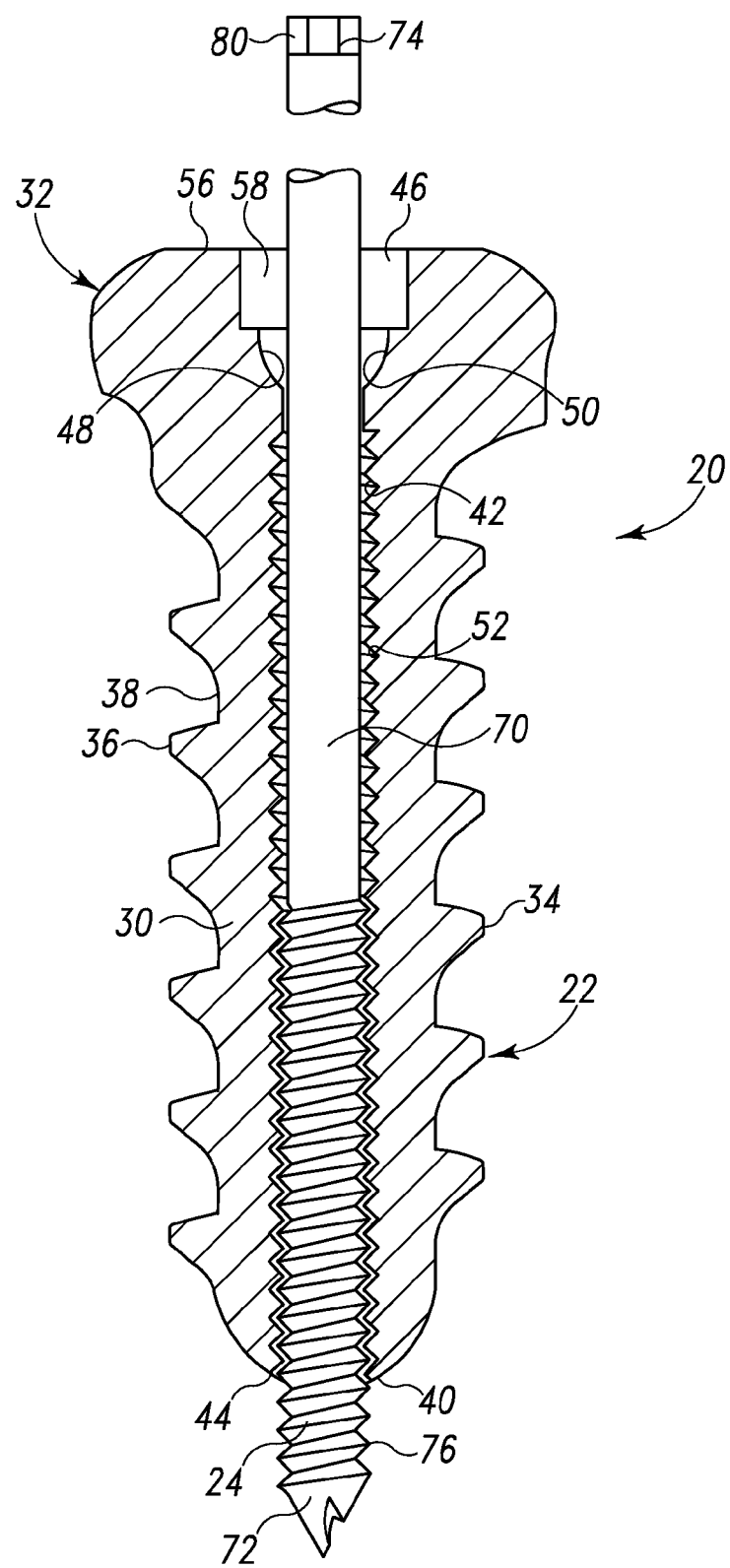
FIG. 5 is a part cross-sectional view of a threaded rod as seen in FIG. 4 threaded into a device as seen in FIG. 3B.

Screw 20 as a compression screw (see e.g. FIG. 5) includes an outer implantable member or screw 22 and an inner implantable member 24. As will be discussed further below, inner member 24 fits within outer member 22, and adjustment of one or both members 22, 24 with respect to each other moves bone parts on either side of a fracture or separated bone pieces to a desired position for healing.

Outer member 22 is a screw in this embodiment, having a shaft portion 30 that transitions into a head portion 32. Shaft portion 30 is generally a straight cylinder having an external thread 34. Thread 34 defines a crest 36 (having a crest diameter D1) and a root 38 (having a root diameter D2). Crest diameter D1 is substantially constant along shaft 30, except for the portion approaching the tip 40 of shaft 30, where crest diameter D1 narrows substantially uniformly to a thread end. Root diameter D2 is substantially constant along shaft 30 above tip 40. Thread 34 has a particular pitch, defined as the length along shaft 30 traveled by thread crest 36 during one full revolution of crest 36 around shaft 30. The pitch of thread 34 remains constant along its length, whether in shaft 30 or head 32, so that grooves formed by or that accommodate one part of thread 34 (e.g. in head 32) will allow the rest of thread 34 to be turned through them. In the illustrated embodiment thread 34 is continuous and extends through the entire length of shaft 30 and into head 32. In other embodiments, thread 34 may exist on discrete portions of screw 22, such as a distal portion of shaft 30 and a proximal portion of shaft 30 into head 32, with a non-threaded portion between. Thread 34 is configured as a bone-engaging thread for insertion into and retention within bone tissue.

Figure 3A:
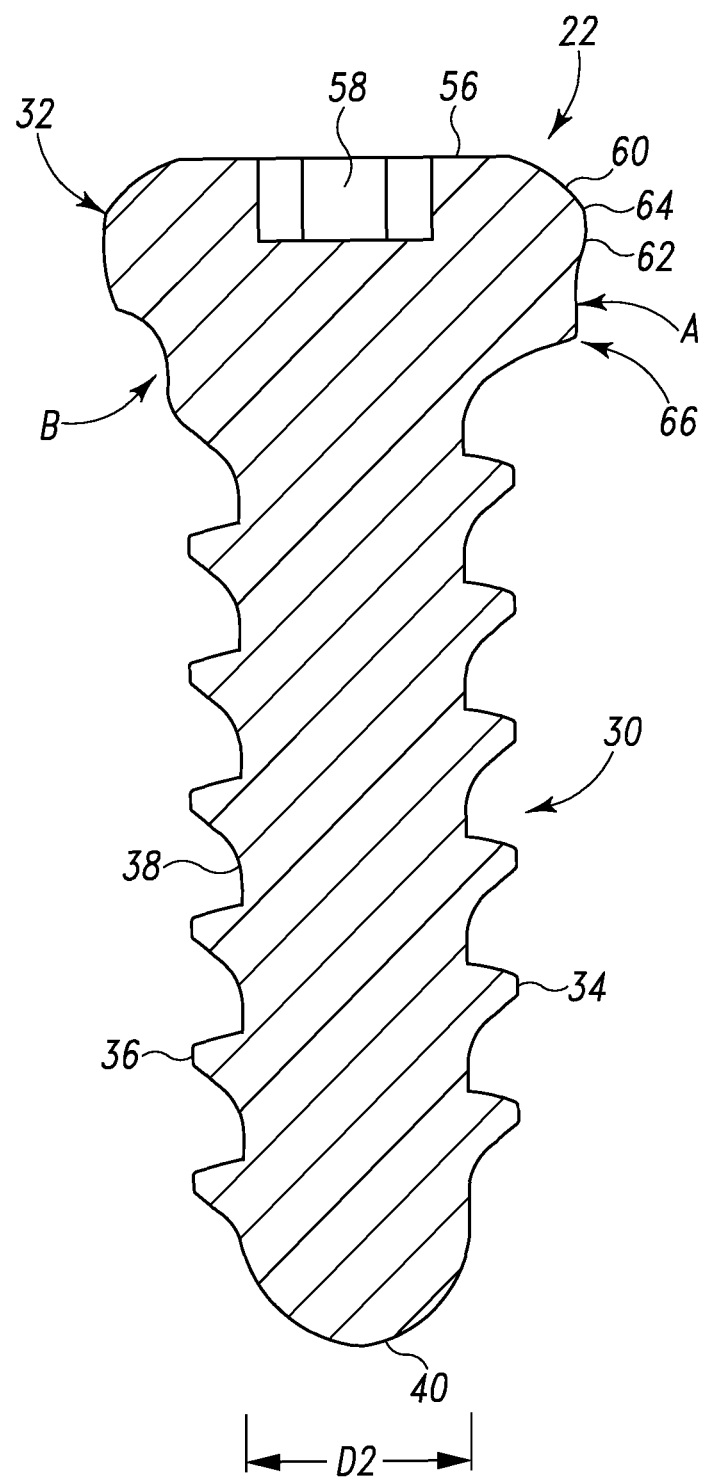
FIG. 3A is a cross-sectional view of a device as seen in FIG. 2 having a non-cannulated core, in the same elevation as seen in FIG. 2 and taken along the plane of the page in FIG. 2 including the central longitudinal axis of the device.
Figure 3B:
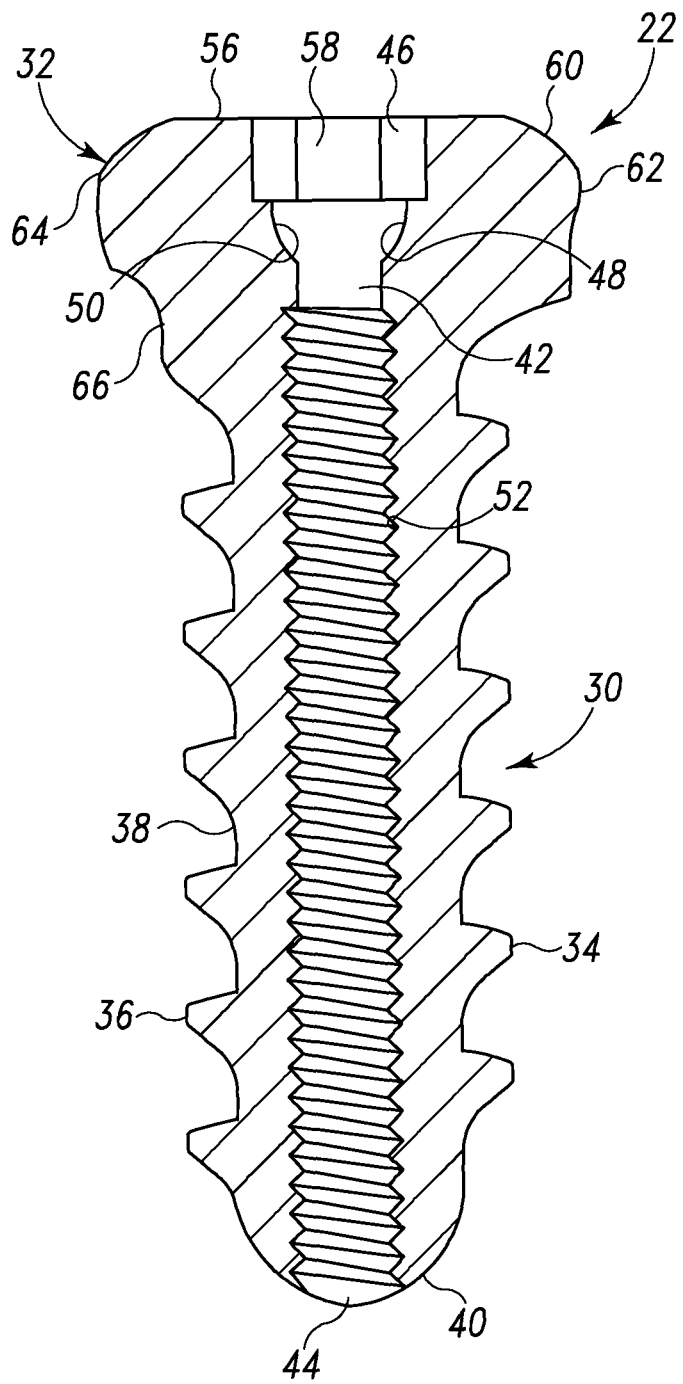
FIG. 3B is a cross-sectional view of a device as seen in FIG. 2 having a threaded interior lumen, in the same elevation as seen in FIG. 2 and taken along the plane of the page in FIG. 2 including the central longitudinal axis of the device.

Shaft 30 is hollow in the embodiment shown in FIG. 3B, having a longitudinal cannula or lumen 42 extending from tip 40 along shaft 30. In a particular embodiment, lumen 42 extends entirely through screw member 22, with a distal opening 44 at tip 40 and a proximal opening 46 through head 32. Lumen 42 has a constant diameter through shaft 30, and in embodiments in which lumen 42 extends through head 32, lumen 42 may have a constant diameter or may vary in diameter. As seen in FIG. 3B, lumen 42 may have one or more outwardly tapering sections 48 and/or a larger cylindrical portion 50. Lumen 42 is at least partially threaded with an interior thread 52 in the illustrated embodiment, which may be a machine thread, and in one embodiment thread 52 extends through all of shaft portion 30. In embodiments in which lumen 42 expands in head portion 32, thread 52 may stop at the point at which lumen 42 extends outward, while in embodiments in which lumen 42 has a constant diameter throughout, thread 52 may extend along the entirety of lumen 42.

Shaft 30 has a length, in the illustrated embodiment, that is consistent with permanent implantation in a long bone, bone piece, or other bone tissue (i.e. a case in which the screw is to be left in the bone following surgery). Thus, its length is such that the entire shaft is within bone tissue, without substantially weakening the bone. In embodiments in which thread 34 extends into head 32 (described further below), at least part of head 32 is lodged in the bone, and so shaft 30 may be relatively shorter than in other cases. In other embodiments, shaft 30 may have a longer length more suited to temporary placement in bone, as will be discussed further below.

Thread 52 has a pitch that is different from the pitch of external thread 34, but turns in the same direction (right-handed or left-handed) as external thread 34. In some embodiments, such as the embodiment of FIG. 3B, the pitch of thread 52 is less than that of thread 34, i.e., there is a shorter distance traveled along lumen 42 in one revolution of thread 52 than is traveled along shaft 30 in one revolution of thread 34. In other words, in such embodiments a full turn of thread 52 travels less distance longitudinally than a full turn of thread 34. In other embodiments, the pitch of thread 52 is greater than that of thread 34. Particular relationships between the pitches of thread 52 and thread 34 can be provided as well. For example, the pitch of thread 52 may be exactly half (or another fraction) that of thread 34 (or conversely, the pitch of thread 34 may be an integer multiple of the pitch of thread 52), so that a revolution of thread 52 travels half the length along lumen 42 as a revolution of thread 34 travels along shaft 30, or in a given length of shaft 30 there are twice as many turns of thread 52 as there are of thread 34. With that relationship, turning outer member 22 with respect to bone and to a stationary inner member 24, as further described below, moves outer member 22 a distance with respect to its bone, but only half that distance with respect to inner member 24.

Head portion 32 is attached to a proximal part of shaft 30, and is preferably unitary or monolithic with shaft 30. In the illustrated embodiment, head portion 32 has a flat proximal surface 56 through which a tool opening 58 extends. Tool opening 58 is sized and configured to accommodate a tool (not shown), such as a driving or gripping tool, and so may be configured as a hexagon, square, Torx®, or other shape conducive to transferring driving torque. The illustrated embodiment of head portion 32 also has an upper side surface 60 and a lower side surface 62 separated by an edge 64. Surfaces 60 and 64 are curved, and each may have a part-spherical curve, but they are not a part of the same spherical curve in that embodiment as seen in the discontinuity of edge 64.

Figure 2:
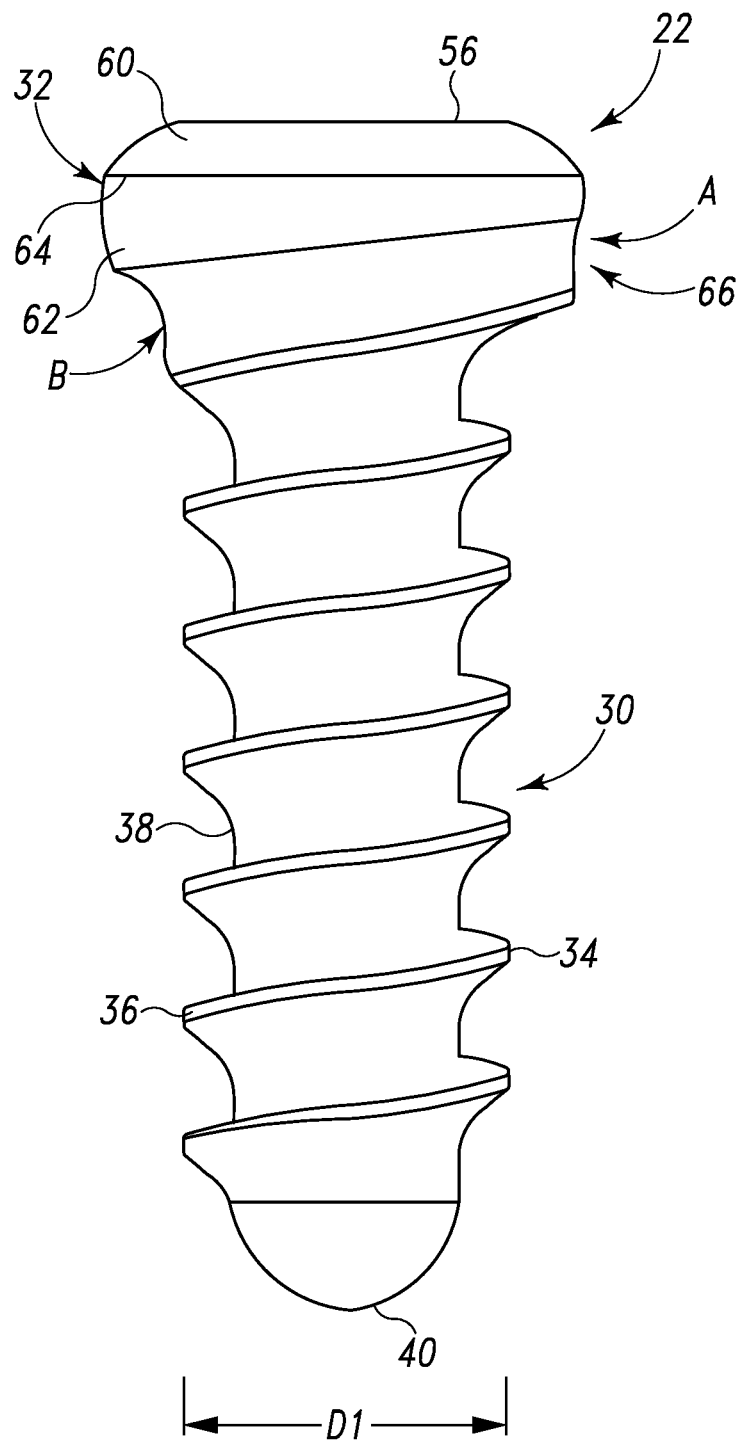
FIG. 2 is a side elevational view of a device according to the present disclosure.

The transition between head 32 and shaft 30 may be a sudden stark change between a spherical surface and a cylinder, as represented in FIGS. 1A and 1B. In that case, the taper or curve from the head to the shaft provides a clear edge between them and the thread runs out on the shaft. It has been found that a better alternative, particularly for pediatric cases, is including a transition area 66 with a continuation of thread 34 into at least the lower side surface 62 of head 32, as represented in FIG. 2. Transition 66 adjoins shaft 30, with its constant root diameter D2, and includes a continuation of crest 36. From a point on head 32, material is removed from head 32, rendering the lower portion of head 32 steadily more narrow as one goes around screw 22. As represented in FIG. 2, head 32 is reduced by a smaller amount on one side (indicated by A) compared to the reduction on the other side (indicated by B). Thus, a point on a path from A to B along the portion of screw 22 visible in FIG. 2 steadily gets closer to the central longitudinal axis of screw 22, i.e., the diameter of the head and/or transition gets uniformly smaller. At the point at which the diameter of the head/transition is equal to the crest diameter D1 of shaft 30, the continuation of crest 36 begins. From that point, crest 36 continues, while the adjacent surface forms a root which continues to decrease in diameter as one goes around screw 22 until the diameter is the root diameter D1 of shaft 30.

Viewed starting from shaft 30, transition 66 continues crest 36 at its constant diameter while root 38 steadily increases in diameter as it goes through the transition from shaft 30 toward head 32. At some point, root 38 has the same diameter as crest 36, and absorbs crest 36. The root 38/crest 36 surface continues to increase steadily in diameter until it meets and blends into surface 62 on head 32.

Thus, in this embodiment head surface 62 steadily narrows with helical travel, getting steadily closer to the center of screw 22 as it travels around screw 22. When its distance from the center of screw 22 is the same as the crest diameter D1 of thread 34, a crest surface 36 begins, which helically winds continuously as part of thread 34. Adjacent crest 36, the surface continues to wind around screw 22 and move steadily closer to the center of screw 22 until the distance from the center of screw 22 is the same as the root diameter D2. At that point, the surface continuously meets and becomes part of root 38 of shaft 30. Considered from the other direction, root surface 38 of shaft 30 begins to get steadily farther away from the center of screw 22 as thread 34 approaches head 32. The increase in root diameter as it winds around screw 22 eventually envelopes or swallows up crest 36 of thread 34. The root surface 38 continues to get farther away from the center of screw 22 as it winds around screw 22 until it reaches the diameter of head 32.

Figure 4:
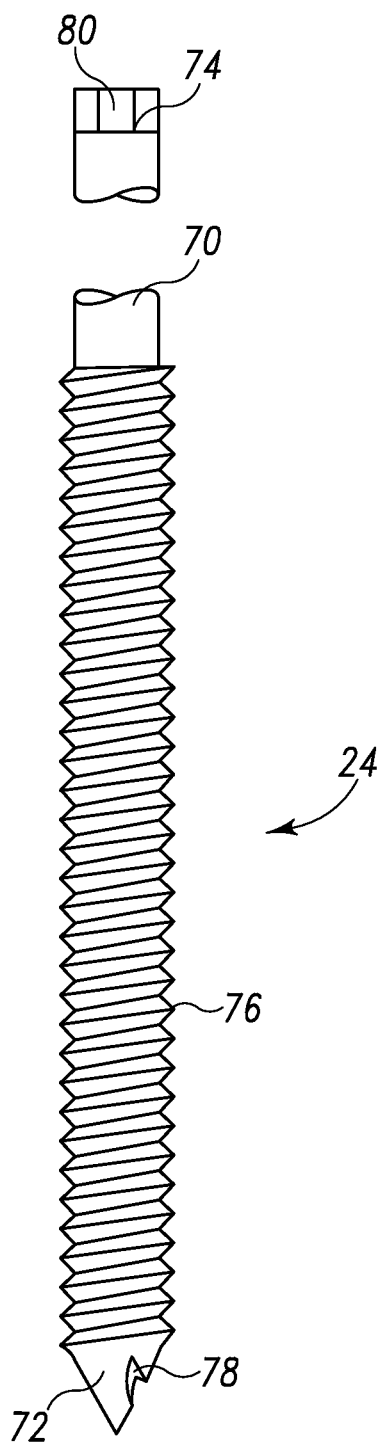
FIG. 4 is an elevational view of a threaded rod.

Internal member 24 is a thin elongated member, which in the illustrated embodiment is a relatively rigid cylindrical rod or pin, and in others may be a flexible or wire-like member. It includes an elongated shaft 70, a distal tip 72, and a proximal end 74. Shaft 70 has an external thread 76 that is compatible with internal thread 52 of screw 22, e.g. having a machine thread of the same pitch, and crest and root diameters that allow interengagement of the respective threads. Tip 72 may have a uniform taper or a cutting edge allowing internal member 24 to be self-tapping. In embodiments in which internal member 24 is a flexible wire or similar member, tip 72 may have anchoring structure such as one or more barbs (e.g. 78 in FIG. 4) or hooks to retain it in bone without having to twist or rotate internal member 24 and thread it into bone. End 74 may have an internal or external print (e.g. hexagonal, square, Torx®, or other configuration) allowing engagement by a screwdriver or other driving tool or by a forceps, clamp or other gripping tool. For example, an external print 80 enables the surgeon to thread internal member 24 into bone, and/or to hold internal member 24 while screw 22 is being rotated, as discussed further below.

Members 22 and 24 are made of durable biocompatible materials, such as stainless steel, titanium, ceramics, certain hard plastics or other sturdy substances. For example, if each is made of stainless steel or titanium, they will each be easily visible in x-rays or other radiographic viewing. In other embodiments, inner member 24 (and/or outer member 22) may be made of resorbable material, so that such piece(s) resorb as or after the bone pieces to which they are connected heal. In particular, it has been found desirable to have inner member 24 be resorbable, so that after screw 20 is used to compress bone parts together and healing is sufficiently begun or completed, inner member can resorb and/or become part of the bone tissue so as to limit or eliminate foreign matter in the body. For example, if inner member 24 enters or crosses an epiphyseal or growth plate in a bone, resorption of inner member 24 may remove the need to take it or other parts out before they negatively impact bone growth in a pediatric patient.

The embodiments discussed above may be used for compression as follows. For purposes of clarity, compression of two separated bone pieces will be discussed. It is understood that the same procedure may be used in situations in which a single bone is fractured or otherwise damaged but not completely separated, and different parts of the bone are to be drawn or held together for healing.

Initially, the surgeon obtains access to the bone pieces to be compressed. Open surgical techniques can be used, and it will be understood that device 20 also lends itself well to percutaneous procedures. Access is gained to two bone parts to be compressed together or moved toward each other. The two pieces may be parts of a long bone with a partial or complete fracture between them, smaller bone parts resulting from trauma, or other fracture or trauma conditions.

Figure 6:
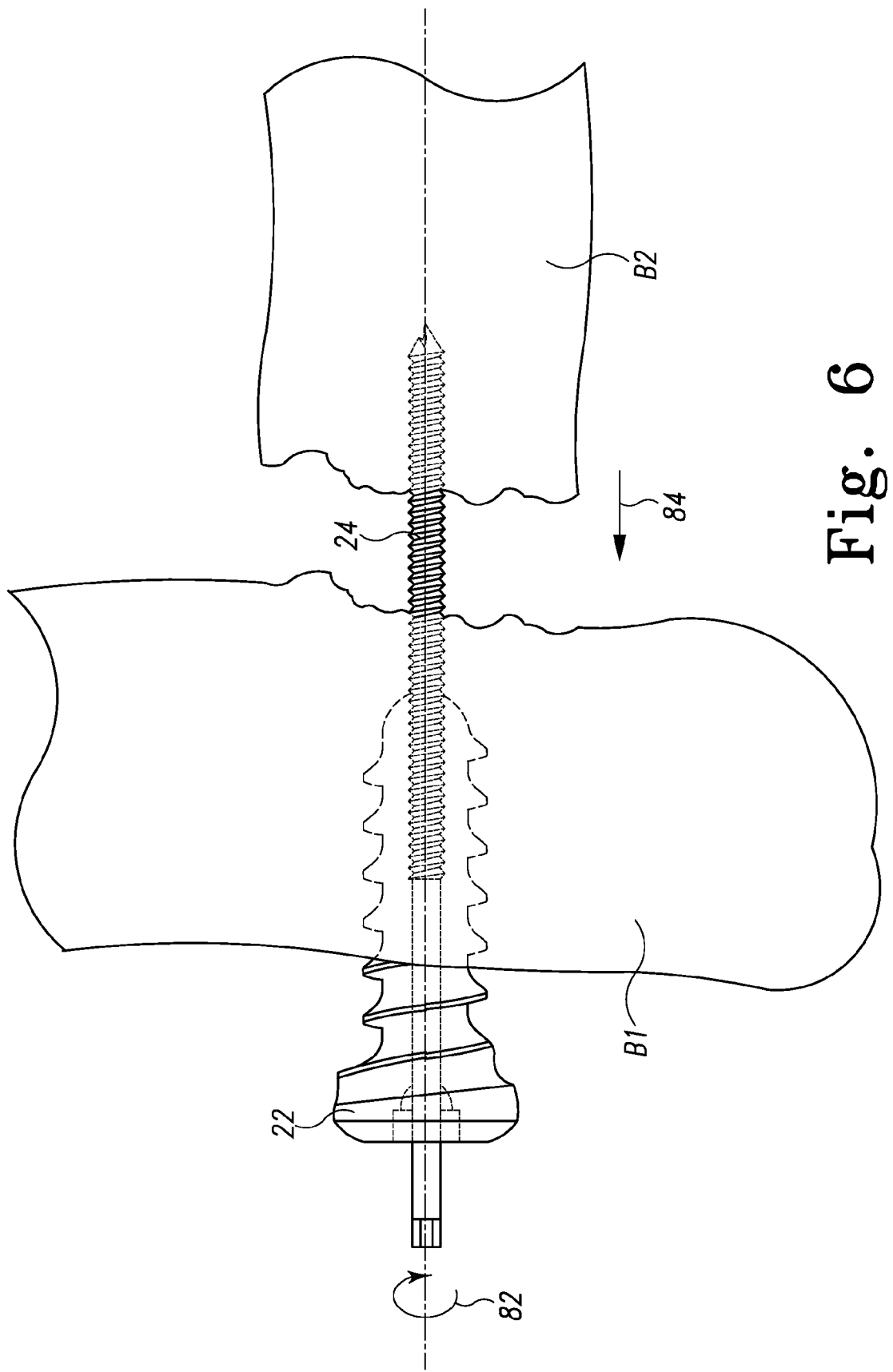
FIG. 6 is a view of the combination of FIG. 5 shown in one type of use.

Once the appropriate surgical access has been achieved, the surgeon drills or otherwise creates a hole through a first, generally more proximal bone piece (e.g. B1 in FIG. 6). At least part of the hole should be sized to allow screw 22 to be threaded into it, and all of the hole should permit internal member 24 to be extended through and move freely within it. A hole is also created in the second, generally more distal bone piece (e.g. B2 in FIG. 6), of a size to allow internal member 24 to be anchored in it. It will be seen that the hole in the second bone piece can be made at substantially the same time as the hole in the first bone piece if a drill bit or other cutting tool having a narrow distal end (compatible with the diameter of internal member 24) and a wider proximal end (compatible with the diameter of shaft 30 of screw 22). Alternatively, after creating the wider hole in the first bone piece, the narrower hole in the second bone piece can be created by inserting a drill bit or other tool through the first bone piece and into contact with the second bone piece. As another alternative, the hole in the second bone piece can be made before or after the hole in the first bone piece, via a separate percutaneous or other surgical opening or path. It will be understood that drill guides of known design can be used to assist in preparing the holes.

Internal member 24 is inserted through the hole in the first bone piece and into the hole in the second bone piece. As previously noted, internal member 24 may be threaded into the second bone piece so that thread 76 engages the second bone piece, or anchored in its hole by barbs, hooks or other anchors. Thus, internal member 24 is anchored to the second bone piece and extends at least partially back through the hole in the first bone piece. Screw 22 is inserted and threaded onto internal member 24, with external thread 76 of internal member 24 engaging internal thread 52 of screw 22. Screw 22 is threaded onto internal member 24 until screw 22 engages the hole in the first bone piece, or alternatively screw 22 is pushed forward to engage the hole in the first bone piece.

Screw 22 is then turned to thread into the hole in the first bone piece. Internal member 24 is kept from turning either through the surgeon holding it (via a gripping or driving instrument engaging internal member 24 or a print on it) or by the interference provided by the hole in the second bone piece, or both. As screw 22 is threaded into the first bone piece (as indicated by arrow 82), it also threads along internal member 24, decreasing the distance between screw 22 and tip 72 of inner member 24 (and thus decreasing the distance between bone pieces, as indicated by arrow 84). With the difference in pitch between thread 34 on one hand and threads 52 and 76 on the other, the relative distance traveled for each revolution between screw 22 and the first bone piece is different from the relative distance traveled between screw 22 and internal member 24 (and the second bone piece to which internal member 24 is attached). For example, if the pitch of threads 52 and 76 is half the pitch of thread 34, then for each revolution of screw 22, screw 22 will travel a distance into the first bone piece that is twice the distance inner member 24 travels along screw 22. Thus, with one turning motion, the surgeon inserts screw 22 into a first bone piece and brings the two bone pieces toward each other. With proper initial measurements, the seating of head 34 of screw 22 in the first bone piece can coincide with a joinder of the two bone pieces.

It will be understood that other steps may also be taken in conjunction with the compression noted above. For example, osteogenic or other therapeutic compositions may be placed between the bone pieces before compression is completed. Further, other implants may be included, such as a plate member (not shown) between head 34 of screw 22 and the bone into which it is threaded.

In embodiments in which thread 34 extends through a transition 66 between shaft 30 and head 32, screw 22 may be threaded further into the first bone piece than would otherwise be possible. The extended thread 34 continues into the bone when turned, so that at least part of head 32 is below the surface of the bone. This allows greater leeway in threading screw 22, and when head 32 is at least partially in bone, screw 22 has greater purchase in the bone and a lower profile, limiting or reducing contact with and damage to adjacent soft tissues.

Once screw 22 has been threaded and the bone pieces are compressed as desired, any remaining amount of inner member 24 that may extend from outer member or screw 22 can be cut off so as to limit or eliminate material outside of or above head 34 of screw 22. Any further work at the surgical site may be completed before closing.

In addition to making compression of bone pieces easier, the disclosed screw 20 also permits easy adjustments in vivo. For example, in pediatric cases, compressing bone pieces together may be necessary in the short term to promote healing. In the longer term, however, it is necessary to allow for growth of bones, particularly the long bones, as the patient gets older. For example, in the case of a fracture to a child's long bone through or adjacent to the growth plates of the bone, implanting compression screw 20 as disclosed above provides support and compression for injured bone. An implantation of another type of screw holds the bone at a given length, and expansion of the bone's growth plate is inhibited, resulting in a lack of growth or perhaps deformity. An implanted screw 20, however, can be revisited by a surgeon to turn inner member 24 with respect to outer member 22 and provide some slack or at least a reduction in the holding force over the growth plate. The growth plate can add mass as in the usual growth pattern, without interference from screw 20. Thus, where normal screws cannot be used in some pediatric cases without impeding growth, screw 20 provides the additional benefit of reducing or eliminating that impedance of growth along with its ease of compression of a fracture.

FIG. 3A shows screw 22 having a solid core (e.g. without threaded lumen 42). It will be understood that lumen 42 of FIG. 3B can be used as a cannulation for passage of a guide wire or similar device or substance, or that a non-threaded cannulation can be provided in screw 22 of FIG. 3A. Embodiments of screw 22 (as seen for example in FIGS. 2, 3A and 3B) can be used by itself or in connection with separate implants in pediatric orthopedic surgery.

The inventors have found that screws having a thread entering into the head as disclosed herein have significant advantages in juvenile or pediatric cases over screws intended for adult patients. Pediatric bones have a cortical wall that is substantially thinner than the cortical wall of adult bones. The underlying spongy (or cancellous) tissue of a pediatric bone is therefore a larger portion of the overall bone than is true of an adult bone.

As already noted, generally orthopedic implants (including screws) used in pediatric cases are merely those made for adult patients, perhaps made for small adults or simply cut down in size. When screws developed for adult patients are inserted into pediatric bone (e.g. FIG. 1B), they are inserted so that the head of the screw is embedded in the cortical bone, so that a minimal amount of the head is above the bone (providing a low profile). A low profile limits or prevents interference with or damage to muscle, ligaments or other adjacent tissue by a screw head. With the thinness of the cortical bone in pediatric patients, such a low-profile placement means that the thread on the shaft of the screw is lodged solely in spongy bone tissue (see FIG. 1B). Further, currently-available screws are machined using common processes developed decades ago, i.e., to make an undercut U (FIGS. 1-2) to allow room for a threading tool used to create the thread to be pulled back without damaging or affecting the head or other part of the screw. As further discussed below, that undercut U is disadvantageous in pediatric cases. Such undercut technology inhibits removal of the screw because the opening O (FIGS. 1-2) cut through the cortical wall of the bone by the screw's thread is wider than the undercut U of the screw. As seen in FIG. 2, such a screw and its threads do not and cannot engage the cortical wall to aid removal.

During healing, bone tissue (a "callous") can grow around the head and in toward the unthreaded neck of the screw. When the time comes to remove the screw, its threads get little or no purchase in the spongy bone and are not in contact with the cortical bone that has grown above the thread crests. The unthreaded undercut through the cortical wall provides no purchase for threading the screw out of the bone. Consequently, turning the screw is less effective or ineffective in moving the screw out of the bone. The screw can be pulled out, through an insertion hole that has become narrower as bone grows toward the shaft and head. Pulling the screw out of the hole breaks off bits of cortical bone as the thread crests are forced through, and the thread crests also carry along an amount of spongy bone. This damage to the bone must be fixed in further steps, as by replacing bone tissue and/or filling with osteogenic or otherwise therapeutic materials.

To try to avoid having to pull screws out, some have sharpened the first thread crest below the screw head. That sharpened thread my make cutting a new groove through new tissue easier, but it does not eliminate the need to cut a new groove. The screw must still be pulled so that the sharpened thread contacts cortical bone, which can result in damage, and then the screw can be turned to try to force the sharpened thread into the cortical bone. There is no guarantee that the thread will be forced into the cortical bone, or that the groove cut will allow the screw to come out of the bone along its longitudinal axis. Sharpening a thread crest on an adult screw does not address these and other issues noted above.

Figure 7:
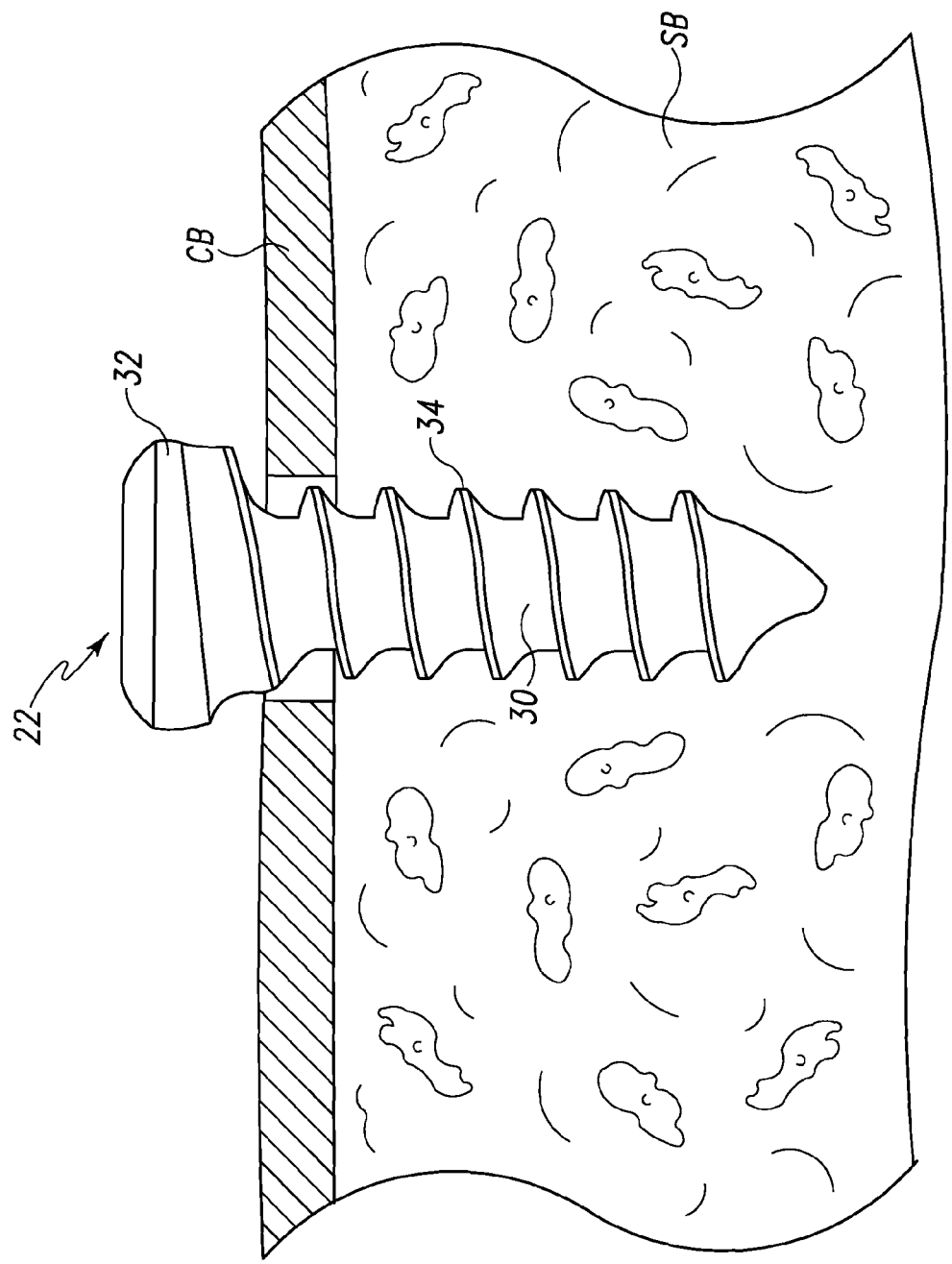
FIG. 7 is a part cross-sectional view of an embodiment of a screw as in FIGS. 2-3B inserted in pediatric bone.

Embodiments such as screws 22 as disclosed herein limit or eliminate such damage. When screw 22 is threaded into pediatric bone its shaft 30 enters spongy bone SB and its thread 34 maintains contact with cortical bone CB when fully threaded into the bone (see, e.g., FIG. 7). When head 32 is seated or fixed with respect to the bone, thread 34 around head 32 is in the cortical portion of the bone, with the crest 36 of thread 34 in associated grooves in the cortical bone. Thread 34 maintains those grooves as new tissue grows. When removal of screw 22 is desired, turning screw 22 in the proper direction results in outward movement of screw 22 because of the engagement of thread 34 with associated grooves in the cortical bone. Any bone that has grown around head 32 or shaft 30 also grows around thread 34. The grooves preserved in the cortical bone by thread 34 provide a path for thread 34 in head 32 and shaft 30 to follow during unscrewing. While some removal of callous or other tissue may be necessary to reach head 32 in order to remove screw 22, no chipping or pulling damage to cortical or cancellous bone occurs when screw 22 is turned for removal. Screw 22 can be unthreaded from the bone completely, resulting in little or no removal of spongy bone or enlargement of the insertion hole, compared to pulling a threaded shaft through a hole smaller than the crest diameter of the thread or forcing a sharpened thread into the cortical bone.

A particular example of the use of a screw such as screw 22 is in the correction of a slipped capital femoral epiphysis (SCFE). SCFE is a condition that affects the hip in pediatric patients, commonly those between the ages of 12 and 16. In this condition, a growth center of the hip (the capital femoral epiphysis) slips backwards on the top of the femur. In a growing child's femur, the epiphyses or growth plates build bone tissue and lengthens the femur. The changes occurring in the growing skeleton during puberty, the fact that the epiphyseal plate is weaker than surrounding bone, and overweight conditions may contribute to the chance of developing SCFE. When SCFE develops, the femoral head fails at the weakest point, through the epiphyseal plate. As a result, a condition similar to a stress fracture occurs. Although non-surgical treatments for SCFE are known, surgery to stabilize and prevent further slippage of the femoral head is preferred.

Figure 8:
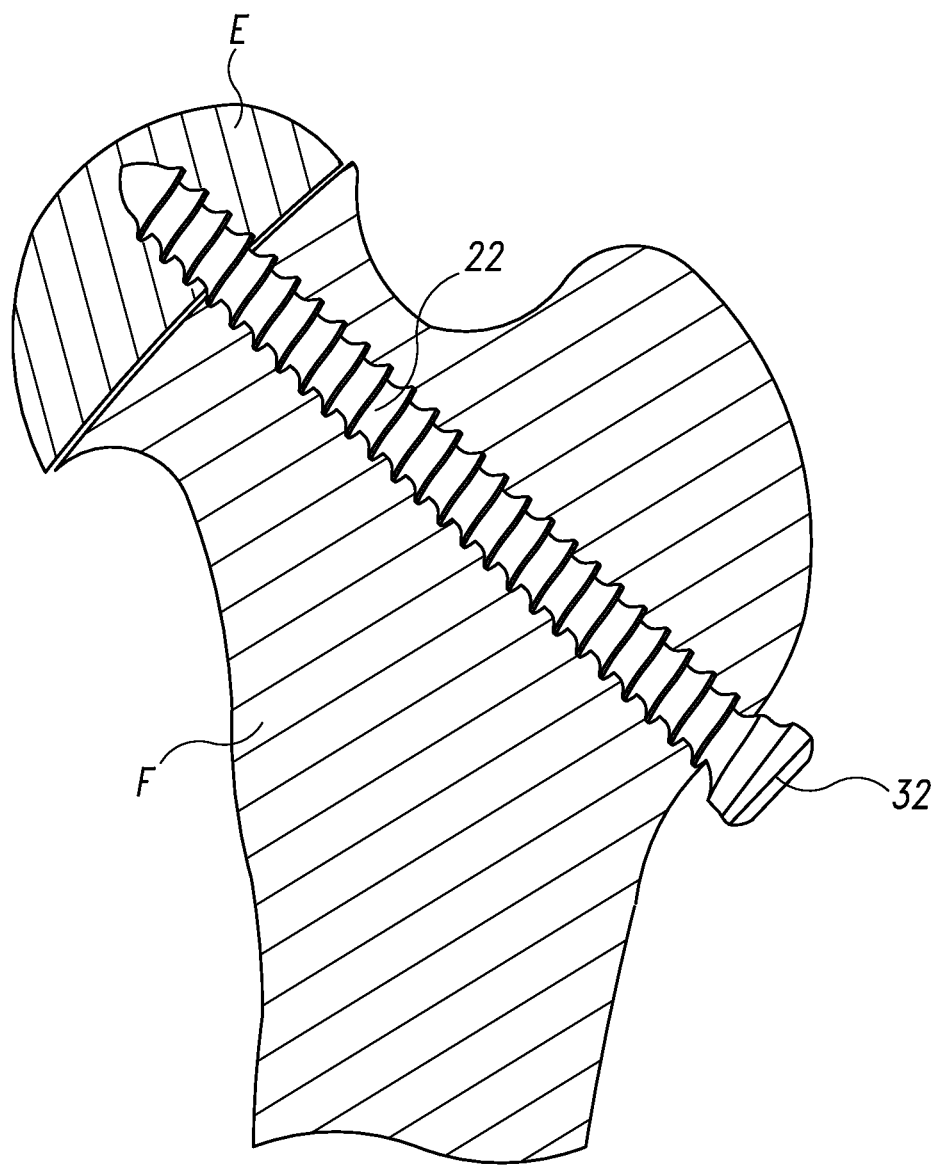
FIG. 8 is a part cross-sectional view of an embodiment of a screw as in FIGS. 2-3B inserted in a femur to correct a slipped capital femoral epiphysis.

One surgical method for correcting SCFE is to place a large screw into the epiphysis to hold it in place. Referring generally to FIG. 8, an embodiment of screw 22 is shown placed through a femur F from an entry point adjacent to or in the greater trochanter. Access to the surgical site is obtained, commonly through a small incision in the thigh, although other access including open surgical procedures can also be used. Under observation (e.g. via x-ray or other viewing device for percutaneous access, or direct where an open surgery is performed), the slipped epiphysis E is adjusted to a normal position with respect to the remainder of the femur and a hole is drilled through the femur, via its metaphysis and into the epiphysis. Screw 22 is threaded into the hole, with its distal end of its shaft 30 entering the epiphysis and head 32 threading into cortical bone in or adjacent to the greater trochanter. Screw 22 holds the slipped epiphysis with respect to the rest of the femur to allow the parts to rejoin.

As noted above, the epiphyseal plate is the growth mechanism of the bone. Layers of new bone cells are formed on the plate, pushing existing tissue outward as the bone grows. While the insertion of screw 22 corrects the SCFE condition, prolonged presence of screw 22 through the epiphyseal plate will prevent normal growth of the bone, since new bone cells in the growth plate cannot move existing tissue against the hold of screw 22. Consequently, after a period sufficient for initial or complete reconnection or healing of the epiphysis to the rest of the femur, screw 22 is removed. As discussed above, screw 22 is easily removed by turning in the appropriate direction, because thread 34 extends into head 32 and remains in contact with cortical bone of the femur throughout its implantation. No pulling of the screw is necessary, which could damage the entry hole through cortical bone, the healed interface between the epiphysis and the rest of the femur, or other parts of the bone.

The above discussion with respect to correction of SCFE is given as a particular example of the advantages of embodiments of screw 22 used alone as described herein. It will be seen that screw 22 or similar embodiments may be used in a variety of pediatric orthopedic situations with similar results. It is further noted that the correction of SCFE as discussed above can be accomplished with a two-piece device 20 as disclosed herein. Inner member 24 can be placed in the epiphysis and through an opening in the femur, and screw 22 (with threaded lumen 42) can be threaded onto inner member 24 and into the femur. In this way, some pressure can be brought to bear between the epiphysis and the rest of the femur as outer member 22 is tightened.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An orthopedic implant for compressing bone parts toward each other, comprising:
a first non-expandable implantable member having a shaft and a head, said shaft having an external thread adapted for anchoring in a first bone part, said external thread extending continuously along a length of said shaft and into a lower part of said head and at least partially along said head toward an upper part of said head, said head having an unthreaded outer diameter larger than a diameter of said external thread, said head having a first radius measured from the longitudinal axis to a first external side of said head that is smaller than a second radius measured from the longitudinal axis to a second external side of said head diametrically opposed to the first side, said first implantable member having a central longitudinal cannula extending through said shaft and said head, said cannula having an internal thread;
a second implantable member having an elongated distal portion and a proximal end, said distal portion having an external thread engaged with said internal thread of said cannula of said first implantable member, said distal portion having a distal end extending from the distal end of said first implantable member and adapted to anchor in a second bone part;
wherein turning said first implantable member threads said first implantable member into said first bone part as well as threading said first implantable member along said second implantable member and moving said distal end of said second implantable member toward said first implantable member.

2. An orthopedic implant for pediatric use, comprising:
a one-piece implantable screw having a shaft with a length and a head proximal of said shaft, said head having an external surface including a part-spherical lower side surface and a proximal surface, said shaft extending from a tip portion to the head, said screw including an external thread adapted to be threaded into bone, said external thread extending continuously along a length of said shaft and into a lower part of said head and at least partially along said head toward an upper part of said head,
wherein said external thread has a crest with a crest diameter and a root with a root diameter, said crest diameter being constant along the entire length of said shaft, said root diameter being constant along said shaft and uniformly increasing in diameter as it travels helically from said shaft to said head, so that said root diameter and said crest diameter coincide at a location on said screw to form a root and crest surface that continues to increase in diameter with helical travel around said screw toward said proximal surface of said head until said root and crest surface blends into said lower side surface, and said lower side surface of said head has a maximum diameter larger than said crest diameter in said shaft, said head having a first radius measured from the longitudinal axis to a first external side of said head that is smaller than a second radius measured from the longitudinal axis to a second external side of said head diametrically opposed to the first side,
wherein when the screw fully implanted in bone, the head is partially threaded into cortical bone with the proximal surface extending from the bone over the surface of the bone for ease of access in removing the screw from the bone.

3. The apparatus of claim 2, wherein said first pitch is greater than said second pitch.

4. The apparatus of claim 2, wherein said first pitch is an integer multiple of said second pitch.

5. The apparatus of claim 1, wherein said head has an outer surface that tapers outwardly from said shaft, and said external thread of said first implantable member has a crest diameter and a root diameter, and wherein said crest diameter remains substantially constant from said shaft and into said head, and said root diameter enlarges substantially uniformly from said shaft as it winds around said head, so that said root diameter and said crest diameter coincide at a portion of said outer surface of said head.

6. The apparatus of claim 1, wherein said second implantable member is a rod.

7. The apparatus of claim 1, wherein said second implantable member is a flexible wire.

8. The apparatus of claim 1, wherein said external thread of said first implantable member is a cancellous thread, and said internal thread of said first implantable member and said external thread of said second implantable member are machine threads.

9. The apparatus of claim 1, wherein said second implantable member is resorbable.

10. A method of moving two bone parts toward each other using the device of claim 1, comprising:
preparing a hole through a first of said bone parts, said hole being of a size to accommodate said first implantable member;
inserting said second implantable member through said hole and into a second of said bone parts so that said distal end of said second implantable member is securely anchored in said second bone part;
threading said first implantable member onto said second implantable member and into said hole in said first bone part, wherein said first implantable member enters said first bone part and said second implantable member moves with respect to said first implantable member to draw said distal part of said second implantable member toward said first implantable member, thereby drawing said bone parts together.

11. An orthopedic implant for pediatric use, comprising:
a one-piece implantable screw having a shaft with a length and a head proximal of said shaft, said head having an external surface including a part-spherical lower side surface and a proximal surface, said shaft extending from a tip portion to the head, said screw including an external thread adapted to be threaded into bone, said external thread extending continuously along a length of said shaft and into a lower part of said head and at least partially along said head toward an upper part of said head,
wherein said external thread has a crest with a crest diameter and a root with a root diameter, said crest diameter being constant along the entire length of said shaft, said root diameter being constant along said shaft and uniformly increasing in diameter as it travels helically from said shaft to said head, so that said root diameter and said crest diameter coincide at a location on said screw to form a root and crest surface that continues to increase in diameter with helical travel around said screw toward said proximal surface of said head until said root and crest surface blends into said lower side surface, and said lower side surface of said head has a maximum diameter larger than said crest diameter in said shaft, said head having a diameter that is smaller than a diameter, wherein when fully implanted in bone, the head is partially threaded into cortical bone with the proximal surface extending from the bone over the surface of the bone for ease of access in removing the screw from the bone.

12. The apparatus of claim 11, wherein said screw includes a distal end of said shaft and a proximal end of said head, said distal end having a first central opening and said proximal end having a second central opening larger in diameter than said first central opening, said screw having a cannula connecting said first and second openings, said cannula having an internal thread.

13. The apparatus of claim 12, further comprising an inner implant having an external thread that is threadable within said internal thread of said cannula, said inner implant having a distal end including an anchor portion to hold said distal end of said inner implant within bone, said distal end of said implant extending beyond said distal end of said shaft.

14. The apparatus of claim 13, wherein said anchor portion includes an external thread adapted for threading into bone, and said implant includes a driving head for imparting rotation to said implant and threading said anchor portion into bone.

15. The apparatus of claim 13, wherein said anchor portion includes a barb.

16. The apparatus of claim 12, wherein said second central opening includes an internal print for accommodating a driving tool, and wherein a non-threaded tapering passage is provided between said internal print and said internal thread of said cannula.

17. The apparatus of claim 11, wherein said head has a maximum diameter that is about twice the root diameter in said shaft.

18. The apparatus of claim 11, wherein an orthopedic plate is held by said screw.

19. The device of claim 1, wherein said cannula of said first implantable member extends from an opening in said head to an opening in said shaft, and wherein said second implantable member is longer than said first implantable member and said first implantable member and said second implantable member have an engaged condition in which said second implantable member extends from both said opening in said shaft and said opening in said head of said first implantable member.

20. The device of claim 1, wherein said second implantable member includes an external print having multiple non-continuous torque transfer surfaces at said proximal end, and said first implantable member includes an internal print having multiple non-continuous torque transfer surfaces.

21. The device of claim 20, wherein said second implantable member includes a smooth portion between said external print and said external thread of said second implantable member.

22. The device of claim 1, wherein said distal portion of said second implantable member includes a portion of said external thread of said second implantable member, so that when implanted said thread engages both the second bone part and the first implantable member, and wherein said external thread of said second implantable member has a substantially constant crest diameter.

23. The apparatus of claim 11, wherein at the location where the root diameter and crest diameter coincide, the root absorbs the crest to form the root and crest surface, said root and crest surface increasing in diameter from the location until it blends into the external surface of the head.

24. The apparatus of claim 19, wherein said second implantable member includes a distal cutting tip.

25. The apparatus of claim 19, wherein said proximal end of said second implantable is insertable through said opening in said shaft of said first implantable member.

26. The apparatus of claim 1, wherein the second implantable member is adapted to be turned when the first and second implantable members are fully implanted so as to reduce holding force.

27. The apparatus of claim 1, wherein the first implantable member is non-frangible and linear.

28. The apparatus of claim 1, wherein said head has an upper portion and a lower portion separated by an edge so that said head has a discontinuity at the edge, the upper portion curving away from the edge and the lower portion curving away from the edge, the upper and lower portions not being part of a same spherical curve, and wherein the external thread extends into the lower portion of said head but not past the edge, and wherein when fully implanted the upper portion of the head extends above the level of surrounding bone tissue and the external thread maintains contact with cortical bone.

* * * * *